(12) United States Patent
Brauer

(10) Patent No.: US 8,178,040 B2
(45) Date of Patent: May 15, 2012

(54) SOFTWARE UPDATE FOR A MEDICAL FLUID MANAGEMENT DEVICE

(75) Inventor: Helge Brauer, Gochsheim (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 12/662,895

(22) Filed: May 10, 2010

(65) Prior Publication Data
US 2011/0072422 A1 Mar. 24, 2011

Related U.S. Application Data

(63) Continuation of application No. 10/111,403, filed on May 6, 2002, now abandoned.

(30) Foreign Application Priority Data

Nov. 9, 1999 (DE) .................................. 199 53 837

(51) Int. Cl.
*A61M 1/00* (2006.01)
*A61M 37/00* (2006.01)
(52) U.S. Cl. ....... 422/44; 604/4.01; 604/5.01; 604/6.01; 604/6.09

(58) Field of Classification Search .............. 422/44–48; 604/5.04, 6.09, 6.11, 65–67; 210/645, 646, 210/781, 782, 739, 741, 746, 90, 102, 421, 210/143; 709/217, 219
See application file for complete search history.

(56) References Cited

U.S. PATENT DOCUMENTS

| 5,725,776 A * | 3/1998 | Kenley et al. ................ 210/646 |
| 6,363,282 B1 * | 3/2002 | Nichols et al. ................ 607/30 |
| 6,584,499 B1 * | 6/2003 | Jantz et al. .................... 709/220 |

* cited by examiner

*Primary Examiner* — Leslie Deak
(74) *Attorney, Agent, or Firm* — Jacobson Holman PLLC

(57) ABSTRACT

A medical fluid management apparatus which includes a plurality of processor systems with respectively associated software programs. The fluid management apparatus has a fluid treatment component and/or a fluid source which can be connected to a patient via a fluid line. The processor systems are connected via a data transfer system to a data input apparatus via which an updating of the software programs belonging to the respective processor systems can take place. After actuation of an operating mode switch, a detection system, while taking into account the existing version of the software programs and/or the existing processor systems, determines which software programs have to be loaded via the data input apparatus. The medical fluid management apparatus allows a simple and user-friendly updating of the operating software even with a complex design of the apparatus.

24 Claims, 2 Drawing Sheets

SOFTWARE UPDATE FOR A MEDICAL FLUID MANAGEMENT DEVICE

This application is a continuation application of application Ser. No. 10/111,403, filed May 6, 2002, now abandoned and hereby claims the priority thereof to which it is entitled.

BACKGROUND OF THE INVENTION

1. Field of the Invention

The present invention relates to a medical fluid management apparatus having a plurality of processor systems in which fluid is transported via a fluid line between a patient and a fluid treatment component and/or a fluid source.

In this connection, fluid management apparatus are in particular understood to be apparatus for the leading, treatment and/or distribution of liquids and/or gases.

2. Description of the Prior Art

Many technical medical apparatus of a higher degree of complexity are assembled from individual functional modules. This is increasingly also the case with fluid management apparatus, in particular with fluid treatment apparatus such as haemotherapy apparatus, in which a fluid of a patient is led via a fluid line to a fluid treatment component, treated by the fluid treatment component and returned back to the patient via the fluid line which can be divided into an arterial and a venous branch. A modern haemodialysis unit includes, for example, a dialysate preparation sub-unit, an ultra-filtration unit and a haemotherapy sub-unit. Such a haemotherapy unit is the subject of DE 198 49 787 C1 of the applicant.

Particularly high demands are naturally made on the operating safety of medical fluid management apparatus for the treatment of patient fluids or for the transport of a fluid to a patient. In this connection, it is of advantage if the apparatus consists of part components or modules which are separate from one another and which each have to meet clearly defined objects. Each module has for its own respective object area reserve systems and troubleshooting routines by which it can be ensured that the module can also satisfy its object when another system fails. It has been found that such a troubleshooting functions substantially more reliably than a centrally controlled system.

Another advantage of fluid management apparatus with a modular design is that their respective hardware configuration can be flexibly adapted to the application purpose. For example, additional measurement and monitoring units can be provided at the customer's request. The performance capability of the individual modules can also be coordinated with the type of application.

The different modules of such a fluid management apparatus typically have a plurality of micro-processors. Both the measurement units and the functional units are largely fitted with their own processor systems. Each processor system requires an individual operating software which is stored in a memory belonging to the processor system.

Even if the medical fluid management apparatus is not intended to consist of a plurality of modules, at least two processor systems are often located in the apparatus in this case for safety reasons. A first processor system takes over the actual control tasks, a second process system takes over the monitoring function with respect to the functioning of the first processor system.

The operating system must be replaced or updated from time to time in medical fluid management apparatus. Such a software update can be necessary for a plurality of reasons such as the elimination of implementation errors in the software or a change in or extension of the functional area of the software, for example by adding a new option. Furthermore, changes in the software of such a fluid management apparatus can result due to customer requests or to general technical or medical progress.

The design of a medical fluid management apparatus having a plurality of processor systems now has the disadvantage here that the operating software of each processor system has to be individually replaced by the later version. For this reason, it is necessary for the carrying out of a software update in a modern medical fluid management apparatus that specially trained technicians take up work on the medical fluid management apparatus with a plurality of update programs in order to load the software programs required for the respective hardware configuration into the apparatus. Such a manually effected software update is therefore very time consuming and expensive.

Various publications from other technical areas deal with the carrying out of software updates for processor systems. A so-called activation circuit is known from EP 0 457 940 A 1 which can be connected to a monitor in order to load a program code or a test code onto the monitor.

In U.S. Pat. No. 5,800,473, the reprogramming of a cardiac pacemaker is described, wherein different programs or data can be transferred to the cardiac pacemaker in dependence on specific parameters.

In DE 44 14 597 A1 and U.S. Pat. No. 5,155,847, computer networks comprising a central computer are proposed, wherein the central computer manages the software and its updating of the workstations.

A computer network is known from DE 44 04 544 C2 with whose aid target computers can be pre-configured with a prepared operating system which is made available by a supply unit.

SUMMARY OF THE INVENTION

It is the object of the present invention to provide an apparatus which allows the software programs in a medical fluid management apparatus comprising a plurality of processor systems to be updated in a simple and favourably priced manner without only trained technicians being in a position to do this. In addition, the safety aspect should be taken into account that an endangering of a patient connected to the fluid management apparatus by the software updating procedure can be effectively and simply avoided.

This object is solved by a medical fluid management apparatus according to the present invention as more fully described hereinafter.

A medical fluid management apparatus in accordance with the invention, for example a haemodialysis machine, has a fluid treatment component and/or fluid source and a fluid line for the transport of fluid between a patient and the fluid treatment component or fluid source. At least two processors or processor systems are included in the fluid management apparatus which are connected to one another by a suitable system for data transfer. Bus systems such as a CAN bus are in particular suitable for this. In accordance with the invention, a data input apparatus is furthermore connected to the data transfer system, with an updating of the software programs belonging to the respective processors' being able to take place via the data input apparatus. Finally, the apparatus in accordance with the invention has an operating mode switch, which is connected to the at least two processors and which, in a first switch state, switches the processor systems into an operating mode and, in a second switch state, switches the processor systems into a software updating mode. Furthermore, a detection system is provided which is likewise connected to the operating mode switch and to the data transfer system and which, in the software updating mode, while taking into account the existing versions of the software programs and/or the existing processor systems, determines which software programs have to be loaded for which processor systems via the data input apparatus and which initiates the loading of these software programs into the relevant processor systems.

The medical fluid management apparatus in accordance with the invention allows a simple and less costly updating of the software programs belonging to the individual processor systems despite its design comprising a plurality of processor systems. In this connection, it is ensured by the detection system that only the actually required software programs are loaded. Not always all software programs therefore have to be loaded again. In the determination of which software programs have to be loaded, the detection system also takes the respective individual hardware configuration into account.

The operating mode switch further brings about a simple possibility to activate all processor systems simultaneously for a software update. This switch can expediently only be switched from the operating mode into the software updating mode when the processor systems allow this as a result of the operating status with respect to the fluid management. In the software update mode, on the other hand, the carrying out of a fluid treatment or of a fluid transport to the patient is not possible. In this way, an unnecessary endangering of the patient by a software update procedure is avoided.

The medical fluid management apparatus can be used particularly advantageously as a haemotherapy unit such as a haemodialysis unit. In this unit, blood is removed from the patient via an extra-corporal blood circulation, treated extracorporally and returned again. If these units are used in intensive medicine, a simple software update possibility of these very complex units is additionally of advantage since a fast and always updated standby operation can be guaranteed.

The fluid management apparatus in accordance with the operation can, however, also be used in other areas such as in peritoneal dialysis. With so-called peritoneal dialysis cycler units and with peritoneal dialysis units with continuous haemodialysis solution circulation, a machine independently carries out a cyclic or continuous replacement of haemodialysis solution in the abdominal cavity of a patient, with used haemodialysis solution being replaced by fresh or treated haemodialysis solution.

Peritoneal dialysis units and haemodialysis units are also used as home dialysers. There is hardly any alternative to this in particular in remote regions. The employment of technicians only to carry out software updating is particularly expensive and time consuming in these cases. The design of the fluid management apparatus in accordance with the invention in accordance with claim 1 also makes it easier in this case that the patient can also carry out the software update himself.

If a reading apparatus for interchangeable mass memories such as CD discs, DVD discs or other data carriers is provided as the data input device, then it is possible to insert, for example, only a single CD into the reading apparatus on which all or a plurality of software versions possible for the relevant medical fluid management apparatus for different apparatus configurations are stored. Every single processor system can thus be updated by means of one single CD with a plurality of update programs so that the separate updating of the respective processor systems by means of separate CDs is superfluous. In this case, it is no longer necessary that trained technicians have to carry out the updating of the software on site, with conventionally different updates having to be carried out with different boundary parameters depending on the unit type.

In this connection, the data input apparatus can also be a part of a processor system. For instance, a processor system can, for example, be suitable to control all input and output elements such as a keyboard, a monitor, etc. as well as the external data communication by means of the data input apparatus.

It is possible in accordance with the invention to distribute, e.g. to send by post, data carriers, which are comparatively cheap to manufacture, such as a CD with the respective latest software version, to the individual users so that a user only has to insert the CD received or a corresponding data carrier into the reading apparatus in order to load the respective latest software version into his medical fluid management apparatus. In this connection, the loading or updating procedure can take place largely automatically after insertion has taken place.

It is also possible to store the whole update software on another storage medium such as a laptop or the like. This storage medium must then be connected to the data input apparatus of the medical unit in order to carry out a desired software update. After the update has taken place, the storage medium can be again separated or removed from the medical fluid management apparatus in order to update another medical fluid management apparatus.

It is furthermore possible for the update software of the data input apparatus to be communicated via the Internet or via remote transfer signals such as radio or infrared. The individual processor systems can also be brought to the latest software status in each case by only one procedure with this embodiment of the invention, since all update programs can be loaded directly after one another in one step.

The detection system of the apparatus in accordance with the invention can be provided as a separate processor system or as part of an existing processor system which additionally takes over this task. In an embodiment especially adapted to a modular design, the detection system is divided into a plurality of detection systems which are located in each of the processor systems and which are only responsible for these. By activating the software updating mode, each processor system then detects independently that new software is available at the data input apparatus and that it has to check and start its own updating procedure.

In accordance with a preferred embodiment, codes of the existing software programs are stored in the detection system, with these codes in particular being able to be version numbers and/or the respective version date. By a comparison of these codes with the program versions on the update storage medium, the detection system can determine whether the existing software version has been superseded or not.

In accordance with another preferred embodiment, codes of the existing hardware configuration are stored in the detection system. By a comparison of these codes with the update software programs made available, for example, by CD, the suitable software programs for the respective hardware configuration can be determined and loaded. It is thereby precluded that software actually used for another unit type is loaded, which is very important with respect to the high safety requirements with fluid management apparatus.

In accordance with another preferred embodiment, a code of the preferred language version is stored in the detection system. Advantageously, the whole apparatus software is contained directly in a plurality of languages on the storage medium such as the CD. By a comparison of the language code with the update software programs available in different language versions by CD, the detection system can determine the language version suitable for the respective user. The required software programs are then loaded in the corresponding language version via the data input apparatus.

A memory chip or a hard disk can, for example, be provided to store the codes for the hardware configuration, for the existing software programs and for the preferred language version. In an updating procedure, the detection system accesses these codes, with the update being carried out in accordance with these codes. In this way, a fully automatic update is made possible which no longer requires any technical knowledge of an operator. This corresponds, so to say, to a so-called plug-and-play function of the software updating procedure itself: After, for example, a CD with the current software has been inserted into the data input apparatus and after the operating mode switch has been switched into the software updating mode, the software updating processes run automatically without any further intervention being required.

In an updating of the software, the documentation of the software or of the medical fluid management apparatus can advantageously be modified or adapted by information stored on the data carrier. In this connection, the updating of the documentation data likewise takes place via the data input apparatus. In this way, after the update has taken place, the information useful for a user with respect to the new software can be made available. This can take place, for example, by the output of corresponding information on a display apparatus such as a monitor which is usually anyway present, with a user being able to work easily with the updated software by a correspondingly commentated menu management. In particular, information can be output on new performance features. Furthermore, information with respect to technical documents, manuals, available spare parts or similar can be stored on the data carrier. Furthermore, it is ensured by the simultaneous loading of the updated software programs and the associated documentation that the user makes use of the respective current documentation. This is also important due to the safety aspects, in particular with medical fluid management apparatus.

In a further advantageous aspect of the invention, the documentation data are loaded in the language version preferred by the user. The preferred language can be determined by means of the code stored in the detection system.

A display apparatus is advantageously provided in the medical fluid management apparatus which can show a hardware configuration and/or version information of the software used. This display apparatus is either part of an existing processor system or directly connected to the data transfer system. For example, it can be shown by means of a monitor which processor systems are actually included in which configuration in the medical fluid management apparatus and which the used software versions are, with, for example, the date information or updating data of the respective last software updates carried out can be activated and displayed.

It is of advantage if the display apparatus is suitable to be able to output the information relating to the loading procedure. The medical fluid management can furthermore include confirmation means to confirm the loading procedure or parts of the loading procedure which are part of a processor system or are directly connected to the data transfer system.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
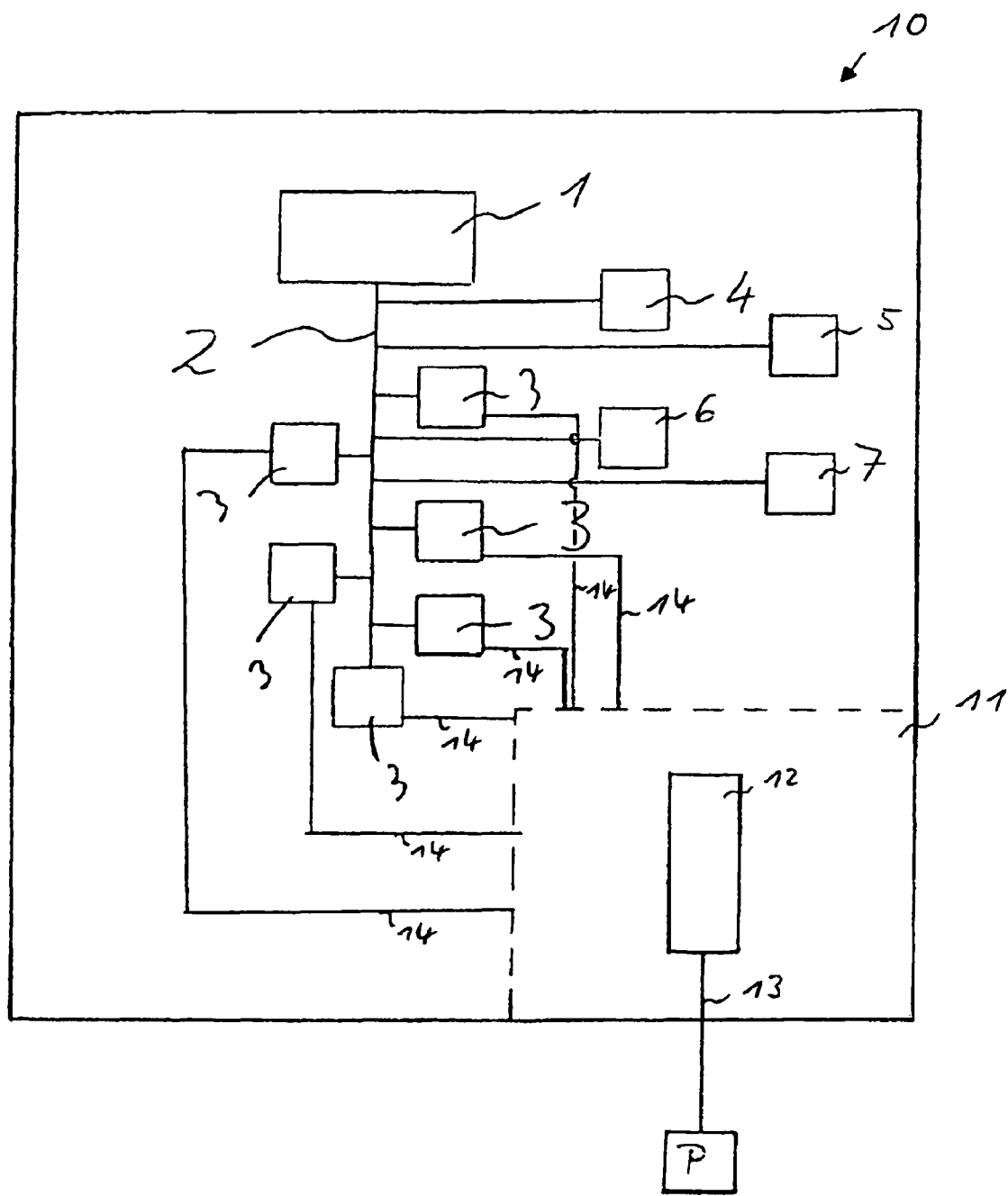
FIG. 1 is a simplified block diagram of a first embodiment of a medical fluid management apparatus in accordance with the invention having a plurality of processor systems.

A first embodiment of a medical fluid management apparatus 10 in accordance with the invention is represented in FIG. 1. In this connection, only the components are shown schematically which are relevant for the understanding of the invention. The further design of such apparatus is known to one skilled in the art familiar with such apparatus. For example, German patent application 198 49 787 of the applicant shows such an apparatus as a haemodialysis unit, to whose disclosure reference is herewith expressly made.

The medical fluid management apparatus, for example a fluid treatment unit such as a haemodialysis unit, has a plurality of processor systems 3 which are connected to one another by a data transfer system 2. A data input apparatus 1 and a software/hardware detection apparatus 4 are connected to the data transfer system 2.

Furthermore, an operating mode switch 5 is connected to the data transfer system 2 and thus to the processor systems 3. The operating mode switch has at least a first switch state and a second switch state which define an operating mode and a software updating mode respectively. In this connection, the operating mode switch 5 is formed as a manual switch. However, it is also possible to realise the operating mode switch 5 as part of the software, i.e. to design a change between the two switch states as part of a running program. It can also be provided for the operating mode switch to be conceived as a remote control. In this case, additional actuating means should be present on site.

Moreover, a display apparatus 6 and confirmation means 7 are connected to the data transfer system 2.

Moreover, a part 11 of the fluid management apparatus 10 is represented symbolically which shows a fluid treatment component 12 which is connected via a fluid line 13 to a patient P. In the case of a haemodialysis unit, the fluid treatment component 12 is a haemodialyser and/or a haemofilter. The fluid line 13 then represents the extra-corporal hose system with which blood is transferred from the patient P to the haemotherapy component 12 and back.

The processor systems 3 are connected to the part 11 of the fluid management apparatus 10 via lines 14 which lead to sensors and/or actors not shown in more detail. These sensors and/or actors monitor and/or control the fluid treatment or the fluid transport. In the case of a haemodialysis unit, on the other hand, these sensors and/or actors monitor and/or control the transport of the blood from the patient to the haemotherapy component 12 and back and the actual haemotherapy itself. With respect to examples in this case for these sensors and/or actors, reference is explicitly made to the medical haemotherapy unit having a plurality of processor systems disclosed in DE 198 49 787 C1.

It is also conceivable that the lines 14 are designed as part of the data transfer system 2, i.e. the sensors and/or actors are selected or read by the processor systems 3 via the data transfer system 2.

The data input apparatus 1 is formed as a CD drive in this embodiment. If a software update CD is inserted by the user into the data input apparatus 1 and the operating mode switch 5 switched into the software updating mode, the software updating procedure is started automatically by the detection system 4. At the same time, the processor systems 3 switch to a waiting state in order to be optionally provided with a new operating software. In this connection, data with respect to the software versions stored on the data carrier can be read from the CD, for example by the detection system 4, and be compared by the detection apparatus 4 with the actual configuration of the medical fluid management apparatus stored in it in order to determine whether updates relate to processor systems actually used in the apparatus or to their configuration. Furthermore, by a comparison of the data read from the data carrier with data stored in the detection apparatus 4, it can be determined whether the software versions used by the processor systems 3 are still current or have to be updated.

If this is found, then in a second step, the actual update procedure can be initiated by the detection system 4, with the respective most current software versions of the processor systems 3 still using an older software being downloaded and being played into these processor systems 3. The whole system consisting of different processor systems 3 with a plurality of different software versions can thus be brought to the respective latest status with a single updating procedure while using, for example, only a single CD, with especially trained technicians no longer being required for this.

On the display apparatus 6, which represents a monitor anyway present in a number of units, the user is given information on the loading procedure. It is in particular provided that each checking procedure of the individual processor systems 3 is represented and that the playing in of the respective new software is only carried out when the user has confirmed this with the aid of the confirmation means 7. An additional input means can be provided as the confirmation means; however, it is also possible to make use of a frequently present keyboard.

If the medical fluid management apparatus 10 is again switched into the operating mode by the operating mode switch 5 at the end of the software updating procedure, the updated system is thus immediately available for a haemotherapy, for example. In this connection, an automatically started initialisation process can optionally be necessary.

For safety reasons, the operating mode switch 5 can only be switched into the software updating mode when the processor systems 3 allow this on the basis of their status. It should thereby be prevented that an updating procedure is carried out while a patient is connected to the fluid management apparatus and the transport of fluid into and/or from the patient is ongoing.

Figure 2:
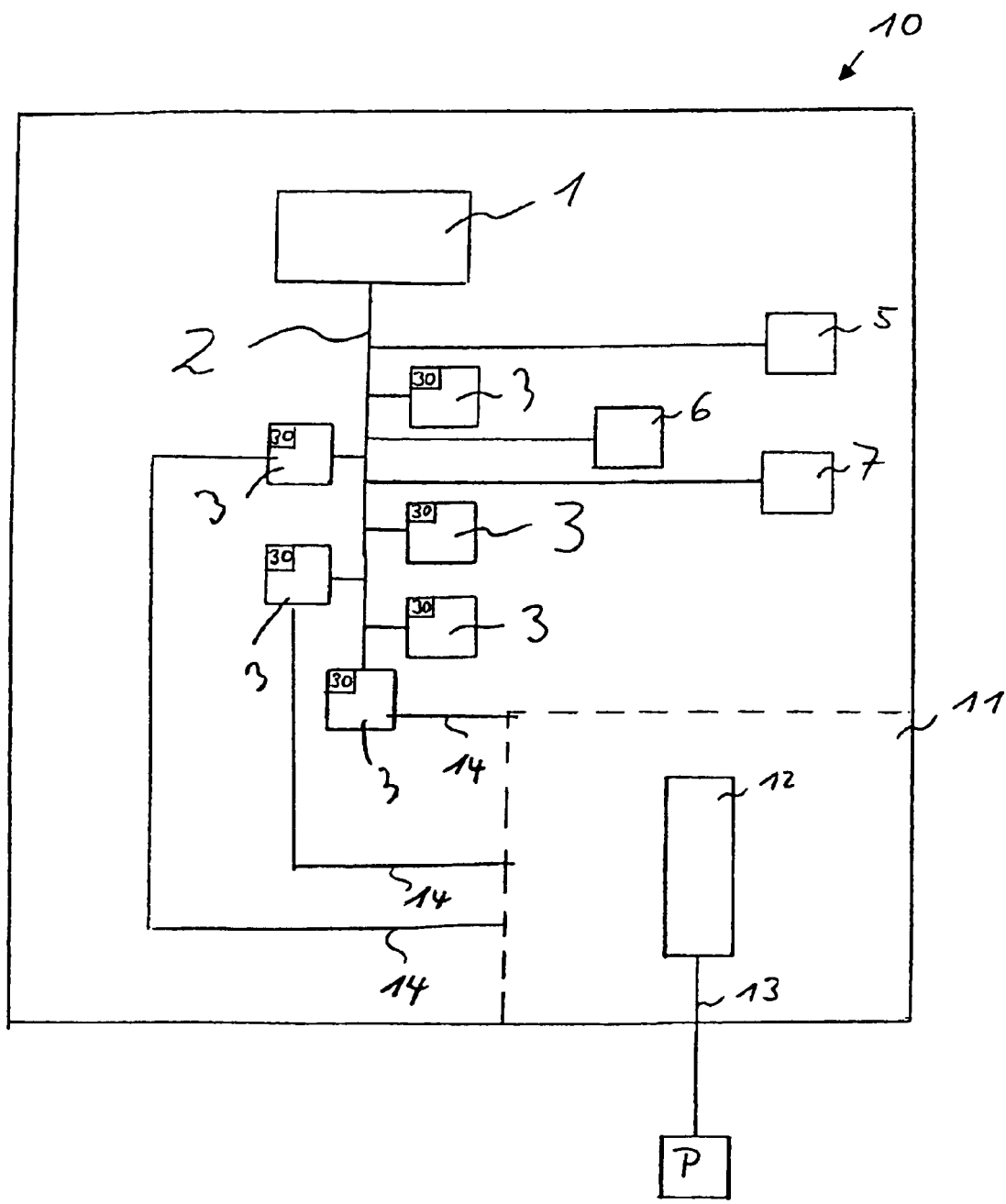
FIG. 2 is a simplified block diagram of a second embodiment of a medical fluid management apparatus in accordance with the invention having a plurality of processor systems.

FIG. 2 shows another embodiment of a medical fluid management apparatus 10 in accordance with the invention which corresponds in large parts to the embodiment shown in FIG. 1. For this reason, the same components in both Figures were provided with the same reference number. The difference between both embodiments is in a different realisation of the detection system 4 which is represented in FIG. 2 as a part 30 of each processor system 3. In this embodiment, the detection system is thus also decentralised.

If, in this case, a user switches on the software updating mode, then this is communicated in turn to the detection system 30 via the data transfer system 2. These now organise completely independently the running of the updating of the operating software similar to the manner set forth above. In this case, each detection system 30 is, however, only responsible for its processor system 3. In this embodiment, the data transfer system 2 is suitable to allow an independent access of the processor systems 3 to the data input apparatus 1 as is in particular possible with a CAN bus. This embodiment has the advantage that the updating function does not depend on the functioning of an individual detection system.

In another respect, reference must be made to the fact that all kinds of modifications of the design of the detection system 4 or 30 in the sense of mixed forms are also possible without departing from the idea of the invention claimed. For instance, the detection system 4 can directly be part of a specific processor system 3. The management of the version numbers and/or data or configuration information do not in this case have to be stored centrally in the one detection system 4. It can be stored locally at each processor system 3, with it being queried in each case individually by the one detection system 4. It is equally possible for the detection systems 30 to be decentralised, but to all access a common data memory which is included in the medical fluid management apparatus 10 and is connected to the data transfer system 2. This can anyway be necessary for the booting procedure of the fluid management apparatus 10 after the switching on if no permanent program memories such as EPROMs are available and the whole software of each processor system has first to be loaded in this phase.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A medical fluid management apparatus comprising:
a) a fluid treatment component and/or a fluid source;
b) a fluid line to transport fluid between a patient and the fluid treatment component and/or the fluid source;
c) at least two processor systems each having its own associated software programs and each having an operating mode in which said processor systems are configured to perform a medical fluid management function within said apparatus, said processor systems line-connected to components of the medical fluid management apparatus to monitor and/or control the fluid treatment and/or fluid transport;
d) a data transfer bus connecting the processor systems;
e) a data input apparatus which is connected to the data transfer bus and via which the software programs belonging to the respective processor systems are updated with externally received software updates;
f) an operating mode switch which is connected to the at least two processor systems and which has a first switch state and a second switch state, said operating mode switch being configured to switch the processor systems into said operating mode in said first switch state and into a software updating mode in said second switch state; and
g) a central detection system which is connected to the operating mode switch and to the data transfer bus, said central detection system, when in the software updating mode, being configured to take into account existing versions of the software programs and/or existing processor systems to determine which of said software updates input via said data input apparatus have to be loaded for which processor systems, and to initiate the loading of these software updates into all the relevant processor systems respectively.

2. The medical fluid management apparatus in accordance with claim 1, wherein the fluid is blood.

3. The medical fluid management apparatus in accordance with claim 2, wherein the fluid treatment component is a haemodialyser and/or a haemofilter.

4. The medical fluid management apparatus in accordance with claim 1, wherein the central detection system includes a processor system.

5. The medical fluid management apparatus in accordance with claim 1, wherein the data input apparatus is a reading apparatus for an interchangeable data memory including CDs or DVDs, said interchangeable data memory configured with update software programs available for said medical fluid management apparatus.

6. The medical fluid management apparatus in accordance with claim 1, wherein the data input apparatus is a receiver apparatus or an interface configured to receive externally stored data.

7. The medical fluid management apparatus in accordance with claim 1, wherein the central detection system includes an apparatus configured to store codes of the existing software programs belonging to the respective processor systems and a configuration thereof, with the codes being version numbers and/or respective version data, said central detection system being configured to compare said codes with update software programs available on said interchangeable data memory to determine whether said update software programs pertain to said processor systems and their particular configuration and, if so, whether said existing software programs are current or need to be updated.

8. The medical fluid management apparatus in accordance with claim 1, wherein the central detection system includes an apparatus configured to store a code of an existing hardware configuration.

9. The medical fluid management apparatus in accordance with claim 1, wherein the central detection system includes an apparatus configured to store a code of a preferred language version.

10. The medical fluid management apparatus in accordance with claim 1, wherein the central detection system is configured to determine which language version of the software programs has to be loaded via the data input apparatus.

11. The medical fluid management apparatus in accordance with claim 1, wherein an updating of documentation data belonging to the software programs can take place via the data input apparatus.

12. The medical fluid management apparatus in accordance with claim 11, wherein the central detection system is configured to determine which language version of the documentation data has to be loaded via the data input apparatus.

13. The medical fluid management apparatus in accordance with claim 1, further comprising a display apparatus which is part of a processor system or is directly connected to the data transfer system.

14. The medical fluid management apparatus in accordance with claim 13, wherein the display apparatus is configured to output information on the loading of said software updates.

15. The medical fluid management apparatus in accordance with claim 13, wherein the display apparatus is configured to display a confirmation query with respect to loading procedures of individual processor systems and wherein the medical fluid management apparatus furthermore includes a confirmation device that is part of a processor system or directly connected to the data transfer bus with which the loading procedures have to be confirmed by a user before loading.

16. The medical fluid management apparatus of claim 1 wherein said processor systems are line-connected to said components of the medical fluid management apparatus by said data transfer bus.

17. The fluid management apparatus of claim 1 wherein said operating mode switch is a software switch.

18. A medical fluid management apparatus comprising:
  a) a plurality of functional modules within said apparatus that include a fluid treatment component and/or a fluid source;
  b) a fluid line to transport fluid between a patient and the fluid treatment component and/or the fluid source;
  c) a plurality of processor systems each having its own associated software programs and an operating mode that pertains to operation of one or more of said plurality of functional modules, said processor systems line-connected to one or more of said plurality of functional modules;
  d) a data transfer bus connecting the processor systems;
  e) a data input apparatus which is connected to the data transfer bus and which is configured to receive software updates for the software programs belonging to the respective processor systems of said medical fluid management apparatus functional modules;
  f) an operating mode switch which is connected with the processor systems and which has a first switch state and a second switch state, said operating mode switch being configured to switch the processor systems into said operating mode in said first switch state and into a software updating mode in said second switch state; and
  g) a detection system within each processor system and connected with the data transfer bus, said detection system, when in the software updating mode, being configured to compare existing versions of the software programs and/or its existing processor systems with software updates received by said data input apparatus to determine which of said software updates input via said data input apparatus have to be loaded for its processor system, and to initiate the loading of these software updates into its processor system.

19. The modular medical fluid management apparatus in accordance with claim 18, wherein said apparatus has a modular design with a flexibly adaptable hardware configuration, said detection system being configured to take said hardware configuration into account when comparing existing software program versions with said software updates received by said data input apparatus.

20. The modular medical fluid management apparatus of claim 18 wherein said processor systems are line-connected to said one or more of said plurality of functional modules by said data transfer bus.

21. The fluid management apparatus of claim 18 wherein said operating mode switch is a software switch.

22. The modular medical fluid management apparatus of claim 18 wherein said data input apparatus includes an interchangeable data memory for storing said software updates.

23. A medical fluid management apparatus comprising:
  a) a fluid treatment component and/or a fluid source:
  b) a fluid line to transport fluid between a patient and the fluid treatment component and/or the fluid source:
  c) at least two processor systems each having its own associated software programs and each having an operating mode in which said processor systems are configured to perform a medical fluid management function within said apparatus, said processor systems line-connected to components of the medical fluid management apparatus to monitor and/or control the fluid treatment and/or fluid transport:
d) a data transfer bus connecting the processor systems, wherein said data transfer bus is a CAN bus:
e) a data input apparatus which is connected to the data transfer bus and via which the software programs belonging to the respective processor systems are updated with externally received software updates:
f) an operating mode switch which is connected to the at least two processor systems and which has a first switch state and a second switch state, said operating mode switch being configured to switch the processor systems into said operating mode in said first switch state and into a software updating mode in said second switch state: and
g) a central detection system which is connected to the operating mode switch and to the data transfer bus, said central detection system, when in the software updating mode, being configured to take into account existing versions of the software programs and/or existing processor systems to determine which of said software updates input via said data input apparatus have to he loaded for which processor systems, and to initiate the loading of these software updates into all the relevant processor systems respectively.

24. A medical fluid management apparatus comprising:
a) a plurality of functional modules within said apparatus that include a fluid treatment component and/or a fluid source:
b) a fluid line to transport fluid between a patient and the fluid treatment component and/or the fluid source:
c) a plurality of processor systems each having its own associated software programs and an operating mode that pertains to operation of one or more of said plurality of functional modules, said processor systems line-connected to one or more of said plurality of functional modules:
d) a data transfer bus connecting the processor systems, wherein said data transfer bus is a CAN bus:
e) a data input apparatus which is connected to the data transfer bus and which is configured to receive software updates for the software programs belonging to the respective processor systems of said medical fluid management apparatus functional modules:
f) an operating mode switch which is connected with the processor systems and which has a first switch state and a second switch state, said operating mode switch being configured to switch the processor systems into said operating mode in said first switch state and into a software updating mode in said second switch state: and
g) a detection system within each processor system and connected with the data transfer bus, said detection system, when in the software updating mode, being configured to compare existing versions of the software programs and/or its existing processor systems with software updates received by said data input apparatus to determine which of said software updates input via said data input apparatus have to be loaded for its processor system, and to initiate the loading of these software updates into its processor system.

* * * * *